United States Patent [19]

Marshall

[11] 4,074,436
[45] Feb. 21, 1978

[54] APPARATUS FOR USE IN SHAPING A TUBULAR DENTAL IMPRESSION ACCESSORY

[75] Inventor: Kenneth Henry Marshall, Castlecrag, Australia

[73] Assignee: Premach Pty. Limited, Sydney, Australia

[21] Appl. No.: 702,962

[22] Filed: July 6, 1976

[30] Foreign Application Priority Data

July 15, 1975  Australia ............................. 2358/75

[51] Int. Cl.² ............................................. A61C 3/02
[52] U.S. Cl. ...................................................... 32/49
[58] Field of Search ................... 32/67, 49, 40 R, 41, 32/42

[56] References Cited

U.S. PATENT DOCUMENTS 472,004   3/1892   Sweet et al. ............................ 32/49

Primary Examiner—Robert Peshock
Attorney, Agent, or Firm—Finnegan, Henderson, Farabow & Garrett

[57] ABSTRACT

Apparatus capable of use by unskilled hands for scribing, including marking and cutting, a tubular sleeve to produce a contoured end corresponding to the contour of the sub-gingival shoulder of a patient's tooth which has been prepared for a jacket crown, which apparatus comprises a mount for a scribing instrument and a body supporting same which is a snug fit within the bore of the sleeve of a pre-prepared jig used to assist the dentist in the tooth preparation, and said scribing instrument is carried by a rotatable portion of the mount to engage and follow a surface on the sleeve which has a contour corresponding to the contour of the sub-gingival shoulder.

3 Claims, 5 Drawing Figures

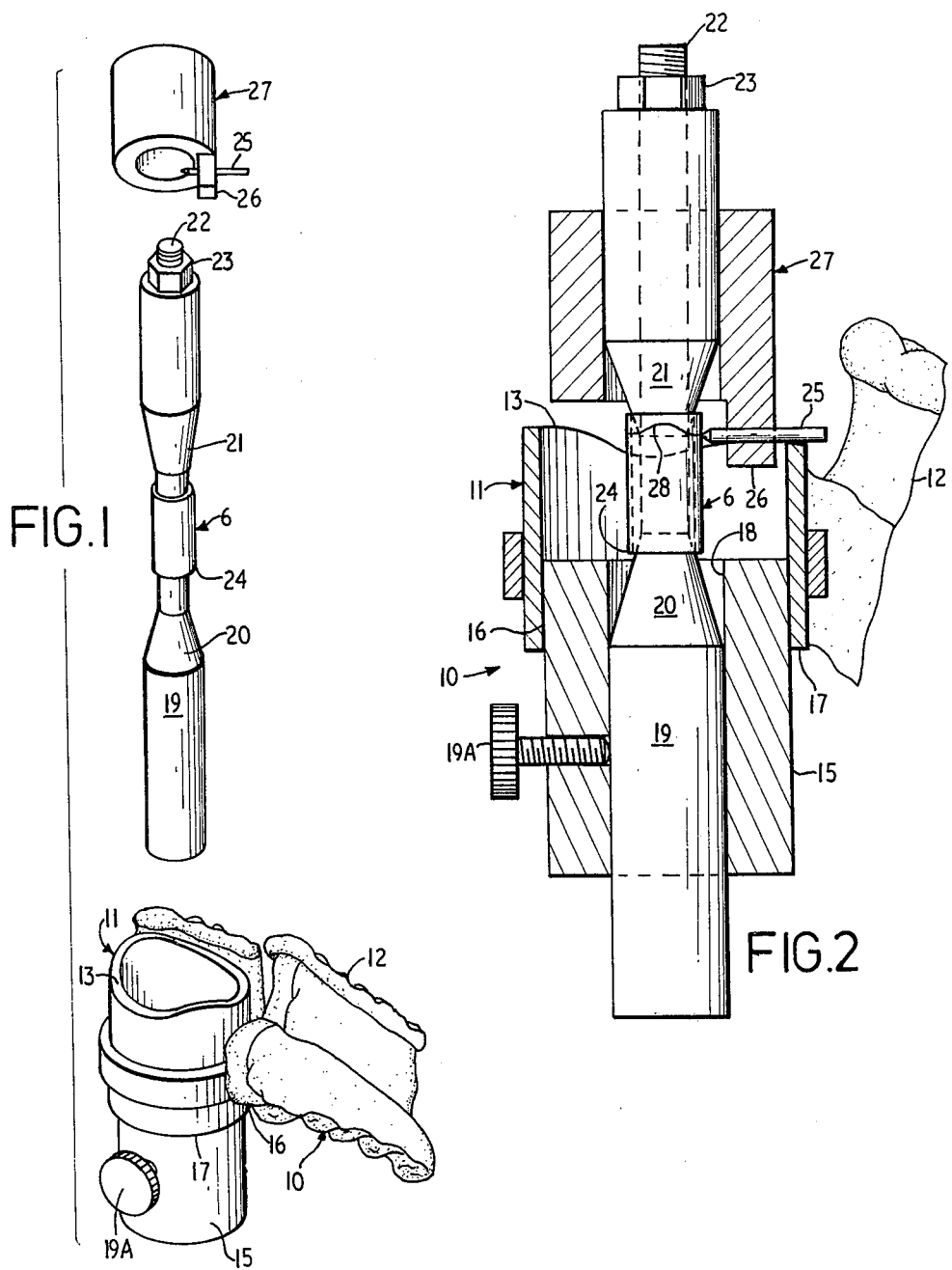

APPARATUS FOR USE IN SHAPING A TUBULAR DENTAL IMPRESSION ACCESSORY

This invention relates to the forming of dental impressions from the jaw of a patient after preparatory work for the fitting of one or more jacket crowns, and more particularly to the apparatus used by a dental mechanic in preparing a tray in which the impression is accommodated.

An instrument has been developed for use by a dental surgeon which greatly assists him in the preparation of a tooth for a jacket crown or for a dental bridge. This instrument incorporates a barrel mounting a diamond bur for radial movement to permit controlled reduction of a tooth, and a mounting sleeve for the barrel. The sleeve is fixed to an overlay to be gripped between the jaws of the patient and has an end cam surface engaged by a follower on the barrel for predetermined control in reducing the tooth structure in the area of the gingiva and for the formation of the necessary sub-gingival shoulder on the tooth. The only free-hand work required of the surgeon is performed on the outer end part of the tooth, such as labio-incisal reduction and outer lingual reduction together with reduction of tooth length. The skill required in the preparation of these outer end parts of the tooth is far less than is necessary in the reduction of the tooth in the area of the gingiva, where an accurate conical angle precisely related to the long axis of the tooth and other teeth is essential and sub-gingival preparation required.

In the use of such an instrument it is necessary for a dental mechanic to prepare an individual jig for the patient for support between his jaws and which accurately mounts a prepared tubular sleeve having an outer end formed with a cam surface. The barrel of the instrument carrying the cutting bur slides and rotates within the sleeve whose axis is accurately related by the mechanic with respect to the long axis of the tooth under treatment, with its cam surface contoured corresponding to the contour of the gingiva about the tooth, thus to provide a simple control for the formation of the sub-gingival shoulder.

It is customary for the dental mechanic after formation of the jig to utilise it together with an instrument to simulate on a model, or case, of the patient's teeth the prepared tooth to be subsequently created by the surgeon in the mouth of the patient himself. As a consequence the dental mechanic is able to provide to the surgeon simultaneously with the jig a tray to accommodate an impression of the patient's teeth including the prepared tooth. Return of the impression to the mechanic will then enable him to design and produce a jacket crown which will be a perfect fit and match within the patient's mouth.

For precision in the impression of the prepared tooth it is customary to fix a copper tube open at both ends in the tray at a position to enclose the prepared tooth with one of its ends contoured and shaped corresponding to the gingival contour about the tooth so as to be a good fit about the tooth even below the gingiva. The tray is positioned firmly within the mouth of the patient by loading it with a quantity of heavy body rubber, while additional rubber is injected from a syringe into the copper tube with sufficient force to build up a compression. Presently, the cutting of an end of the copper tube to the gingival contour before location within the tray is performed manually by trial and error, and a degree of skill is required.

It is the main object of this invention to provide apparatus which will simplify the shaping of the contoured end of a tube for use in an impression tray.

To this end, according to the invention there is provided apparatus to assist in shaping an end of a tubular dental impression accessory corresponding to the shape of the sub-gingival shoulder on a tooth prepared for a jacket crown by a bur controlled in its axial extension by a tubular sleeve with a cam surface at one end, said apparatus comprising a part for mounting with respect to the sleeve, a stem supported by said mounting part within the sleeve, means on said stem for supporting the tubular accessory within the sleeve and confronting the end cam surface thereof, scribing means carried either by the sleeve or a portion of the apparatus, and means for imparting relative rotational movement between the tubular accessory and the marking or cutting means under control of the end cam surface to produce on the tubular accessory a similarly contoured end cam surface.

A preferred embodiment of the invention is illustrated in the accompanying drawings, in which:

FIG. 1 is an exploded perspective view of the jig, the tubular insert and the scribing device;

FIG. 2 is an elevation in section of the assembled components shown in FIG. 1;

Figure 3:
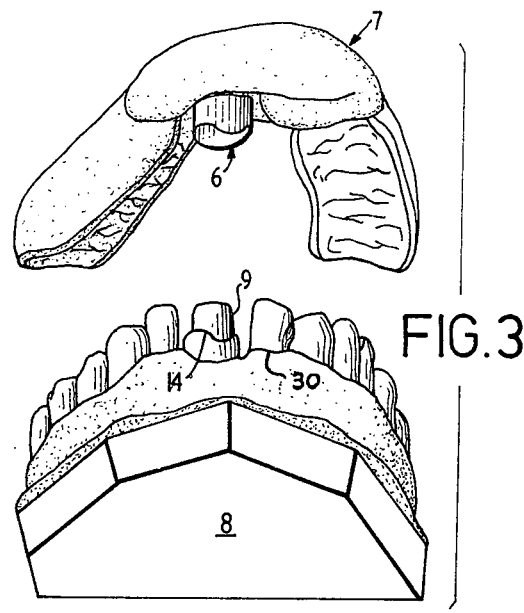
FIG. 3 is an exploded perspective view of a model of the patient's teeth and the tray member with the contoured copper tube inserted therein.

The preferred embodiment of the invention will now be described in which it will be assumed that the apparatus is intended for use in the preparation of a copper tube 6 for incorporation in an impression tray 7 for the forming of a model, or cast, (not shown) of a patient's tooth or teeth prepared with the aid of a dental instrument, as referred to above, for the fitting of a jacket crown. According to conventional practice a model 8 of the patient's teeth has already been constructed by the dental mechanic and the tooth preparation at 9 simulated thereon by the use of a similar dental instrument with a jig 10 pre-formed by the mechanic. As stated above, this jig 10 comprises a tubular sleeve 11 secured in an overlay 12 which one end 13 contoured to a predetermined cam surface corresponding to the gingiva contour 14 about the base of the tooth 9 under treatment. As shown for clarity in FIGS. 3 and 4 the contour 14 appears to be above the gingiva margin 30, but in fact the gingiva about the base of the tooth has been removed to show the shoulder which will be normally located sub-gingivally.

The apparatus consists of a base portion 15 shaped as a cylindrical barrel having means, such as a split skirt 16 to create a jam-fit within the tubular sleeve 11 adjacent the end 17 opposite the cam surface 13. The base 15 is bored as at 18 and a stem 19 is inserted therethrough to extend through the sleeve 11 and beyond its contoured end 13. A pair of confronting centering cones 20 and 21 are supported by cylindrial portions of on the stem 19, at least the outer one 21 of which is slidable thereon to form a stem assembly. A copper tube 6 of pre-selected diameter is located over the stem 19 and between the cones 20 and 21 with the outer end of the stem threaded as at 22 to accept an assembling nut 23 to draw the cones 20 and 21 together and fix the copper tube 6 with respect to the tubular sleeve 11. In its secured position the copper tube 6 is coaxial with the sleeve 11 with only one end 24 extending inwardly of the contoured end 13 of the sleeve 11 and the stem assembly is locked in position by a thumb screw 19A.

Figure 4:
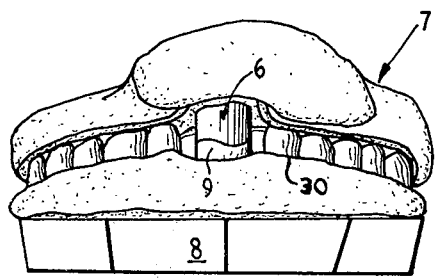
FIG. 4 is a front elevation of the assembled components shown in FIG. 3.
Figure 5:
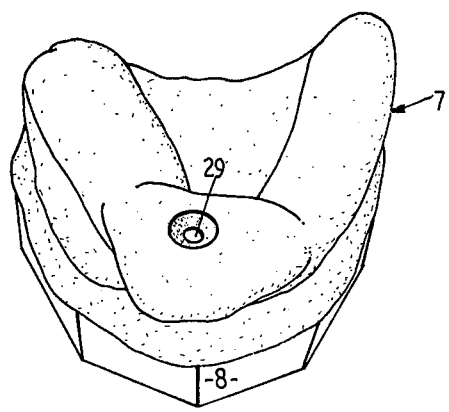
FIG. 5 is a plan view in perspective of the assembled components shown in FIGS. 3 and 4 showing the port through which impression material is inserted in the tray.

A stylus 25, or other scribing, marking or cutting means, is adjustably fixed upon an arm 26 having a mount 27 slidable and rotatable on the stem 19 of the apparatus. The stylus 25, or even an associated cam follower, may then be manually held against the cam surface 13 of the tubular sleeve 11 as shown in FIG. 2 while rotated therearound to scribe, mark or cut as at 28, an end portion of the copper tube 6 to the same contour as the cam surface 13, and therefore the gingival contour 14 about the patient's tooth 9 as well as the sub-gingival shoulder. Subsequently the copper tube 6 may be removed from the apparatus and trimmed, if necessary, before insertion into the impression tray as shown in FIGS. 3 and 4. It has been found that appropriate contouring of the copper impression tube 6 can be effected quickly and accurately by use of the above apparatus and that high quality impressions have resulted. A port 29 is provided in the top of the tray 7 through which impression material can be inserted to obtain an impression of the treated tooth 9.

Whereas a preferred embodiment has been described in the foregoing passages it should be understood that other forms and modifications are possible within the scope of this invention.

What I claim is:

1. In a dental jig for the preparation of a patient's tooth for a jacket crown by which radial reduction and the provision of a contoured sub-gingival shoudler is effected on the tooth by a cutting bur enclosed by a tubular sleeve having a contoured cam surface at a first end which functions to guide the axial extension of the cutting bur to determine the contour of the formed sub-gingival shoulder, apparatus for providing a contoured end on a dental impression tube to correspond said tube end to the contour of said sub-gingival shoulder to permit matching abutment of said tube end to said shoulder when an impression is to be made of the prepared tooth, said apparatus comprising a pair of confronting centering cones between which said impression tube is clamped, a cylindrical portion supporting each said cone, a bored spigot about one of said cylindrical portions and securable in a second end of said tubular sleeve, means for anchoring said one cylindrical portion in said spigot in a position where a portion of said impression tube is located internally of and opposite said contoured cam surface, a collar slidable and rotatable upon the other said cylindrical portion, scribing means engageable with said portion of said impression tube to produce said contoured end and being carried by said collar, and means abutting said contoured cam surface to guide said scribing means during rotation of said collar.

2. Apparatus according to claim 1, wherein said spigot is a jam-fit within said sleeve.

3. Apparatus according to claim 1, wherein said centering cones and said cylindrical portions supporting same are provided as an assembly upon a stem, said one cylindrical portion being formed integrally with said stem, said other cylindrical portion being axially bored and slidable along said stem, and clamping of said impression tube between said centering cones being effected by a nut threaded upon the end of said stem.

* * * * *

UNITED STATES PATENT AND TRADEMARK OFFICE
CERTIFICATE OF CORRECTION

PATENT NO. : 4,074,436
DATED : February 21, 1978
INVENTOR(S) : Kenneth Henry Marshall It is certified that error appears in the above-identified patent and that said Letters Patent are hereby corrected as shown below:

Column 1, line 47, ", or case" should read -- , or cast --.

Column 2, line 51, "overlay 12 which" should read -- overlay 12 with --.

Column 2, line 66, "cylindrical portions of on" should read -- cylindrical portions of --.

Signed and Sealed this

Thirteenth Day of November 1979

[SEAL]

Attest:

RUTH C. MASON
Attesting Officer

LUTRELLE F. PARKER
Acting Commissioner of Patents and Trademarks